United States Patent
Vanneste et al.

(10) Patent No.: US 7,799,944 B2
(45) Date of Patent: Sep. 21, 2010

(54) PROCESS FOR THE PREPARATION OF (METH)ACRYLATE DI-AMMONIUM SALTS AND THEIR USE AS MONOMERS FOR THE SYNTHESIS OF POLYMERS

(75) Inventors: Piet Vanneste, Denderwindeke (BE); Raf Loenders, Bierbeek (BE); Ivan Vanden Eynde, Keerbergen (BE); Sabine Eeckhaoudt, Evergem (BE)

(73) Assignee: Taminco N.V., Ghent (BE)

( * ) Notice: Subject to any disclaimer, the term of this patent is extended or adjusted under 35 U.S.C. 154(b) by 1136 days.

(21) Appl. No.: 10/595,139

(22) PCT Filed: Sep. 6, 2004

(86) PCT No.: PCT/EP2004/052056
§ 371 (c)(1),
(2), (4) Date: Mar. 3, 2006

(87) PCT Pub. No.: WO2005/023754
PCT Pub. Date: Mar. 17, 2005

(65) Prior Publication Data
US 2007/0010591 A1    Jan. 11, 2007

(30) Foreign Application Priority Data
Sep. 5, 2003    (EP)    ................... 03020119

(51) Int. Cl.
    C07C 69/52    (2006.01)
(52) U.S. Cl. ................................ 560/222
(58) Field of Classification Search ........ None
    See application file for complete search history.

(56) References Cited

U.S. PATENT DOCUMENTS

| 7,026,503 B2 | 4/2006 | Nestler et al. |
| 2002/0035198 A1 | 3/2002 | N'Zudie et al. |
| 2002/0183543 A1 | 12/2002 | Riondel et al. |
| 2002/0193545 A1 | 12/2002 | Riondel |
| 2003/0050417 A1 | 3/2003 | Riondel et al. |
| 2003/0100679 A1 | 5/2003 | Riondel et al. |
| 2003/0153675 A1 | 8/2003 | Riondel et al. |
| 2003/0171489 A1 | 9/2003 | Riondel et al. |
| 2003/0191264 A1 | 10/2003 | Crass et al. |
| 2004/0026053 A1 | 2/2004 | N'Zudie et al. |

FOREIGN PATENT DOCUMENTS

| EP | 1 179 552 A1 | 2/2002 |
| EP | 1 253 137 A1 | 10/2002 |
| EP | 1 254 891 A1 | 11/2002 |
| EP | 1 254 901 A1 | 11/2002 |
| FR | 1 529 000 A1 | 6/1968 |
| FR | 1 568 382 | 5/1969 |
| GB | 1174148 | 12/1969 |
| JP | 10-158224 A * | 6/1998 |
| WO | 01/55224 A2 | 8/2001 |
| WO | 01/55226 A2 | 8/2001 |
| WO | WI 01/55089 A2 | 8/2001 |
| WO | WO 01/55088 A2 | 8/2001 |
| WO | WO 01/55225 A2 | 8/2001 |
| WO | 02/12361 A1 | 2/2002 |
| WO | 02/100815 A1 | 12/2002 |

OTHER PUBLICATIONS

Korshunov M A et al: "Alpha-Beta-Unsaturated Esters with Functional Substituents in the Alkoxy Group VII. Acrylic and Methcrylic Esters of Monohybrid Polyamino Alcohols"; Journal of Organic Chemistry of the USSR, vol. 5, No. 11, 1969, pp. 1893-1898.
Patent Abstracts of Japan, vol. 1998, No. 11, Sep. 30, 1998 & JP 10 158224, Nitto Chem Ind. Co., Ltd; Nitto Riken Kogyo KK), Jun. 16, 998.

* cited by examiner

Primary Examiner—Paul A Zucker
(74) Attorney, Agent, or Firm—Sughrue Mion, PLLC

(57) ABSTRACT

The invention relates to the preparation of (meth)acrylate di-ammonium salts responding to formula (I)

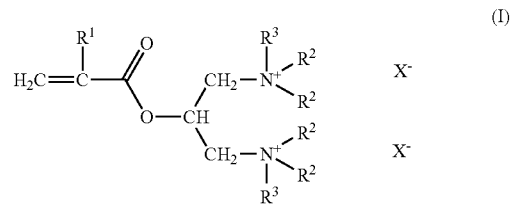

wherein $R^1$ represents hydrogen or methyl, each $R^2$, independently, represents an alkyl comprising from 1 to 4 carbon atoms, each $R^3$, independently, represents an alkyl or an aralkyl and each $X^-$, independently, represents an anion; having a high purity and their use as monomers for the synthesis of polymers useful as cationic flocculants.

25 Claims, 1 Drawing Sheet

PROCESS FOR THE PREPARATION OF (METH)ACRYLATE DI-AMMONIUM SALTS AND THEIR USE AS MONOMERS FOR THE SYNTHESIS OF POLYMERS

FIELD OF THE INVENTION

The invention relates to the selective preparation of (meth) acrylate di-ammonium salts of high purity and their use as monomers for the synthesis of polymers, useful as cationic flocculants.

BACKGROUND OF THE INVENTION (Meth)acrylate ammonium salts and their use as monomers for the synthesis of polymers useful as flocculants have been described in WO 01/55088, WO 01/55089, WO 01/55225 and US2002/0035198. In these publications the (meth)acrylate ammonium salts are synthesised by the reaction of the corresponding di-amine (meth)acrylate with less than 2 equivalents of an alkyl or a benzylhalide in an organic solvent such as chloroform and with the addition of water to remove the produced (meth)acrylate ammonium salt. EP 1 253 137 describes a synthesis were the organic solvent is an acrylate ammonium salt. Again, near the end of the reaction period, water is added to remove the produced salt. These processes yield aqueous solutions of a mixture of a (meth)acrylate di-ammonium salt and a (meth)acrylate mono-ammonium salt. These processes do not permit to isolate (meth)acrylate di-ammonium salts with a high purity. It is also almost impossible to purify the obtained mixtures. When used as monomers in the synthesis of polymers, these polymers will inevitably contain a significant amount of units derived from the mono-ammonium salts. In order to effectively build-in double charged monomers into polymers, the (meth)acrylate di-ammonium salts need to be obtained selectively. In order to be useful as starting material for the production of high molecular weight polymers and copolymers for flocculation, the di-ammonium salts need to be very pure.

SUMMARY OF THE INVENTION

The present invention now provides a process for the selective manufacture of (meth)acrylate di-ammonium salts, and a process for the manufacture of a polymer containing units derived from these (meth)acrylate di-ammonium salts, that overcome the above-mentioned problems.

The present invention therefore relates to a process for the manufacture of a (meth)acrylate di-ammonium salt of formula (I)

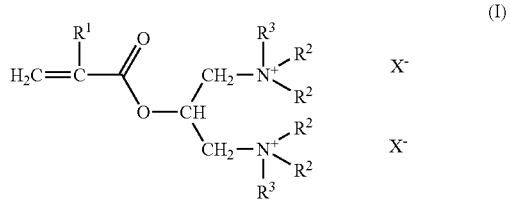

wherein $R^1$ represents hydrogen or methyl, each $R^2$, independently, represents an alkyl comprising from 1 to 4 carbon atoms, each $R^3$, independently, represents an alkyl or an aralkyl and each $X^-$, independently, represents an anion, comprising (a) the reaction of the di-amino-(meth)acrylate of formula (II)

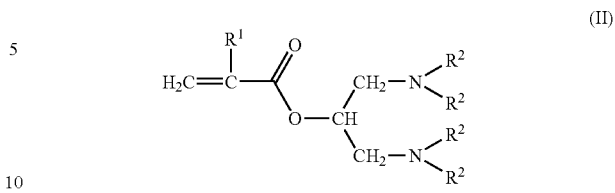

with preferably more than 2 equivalents of at least one alkyl or aralkyl compound of formula $R^3X$ in an organic solvent containing at most 5000 ppm of water and wherein the di-ammonium salt of formula (I) has a solubility at 25° C. of less than 1 g/100 g of solvent and wherein the solubility of the corresponding amino-(meth) acrylate ammonium salt of formula (V)

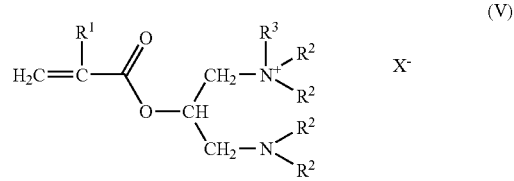

has a solubility at 25° C. of at least 20 g/100 g of solvent; and (b) the separation of the compound of formula (I) from the reaction mixture without dissolving it in water, the compound of formula (I) being separated from the reaction mixture in the form of a solid product comprising the compound of formula (I) and, per mole of this compound, less than 0.1 mole, preferably less than 0.05 mole and more preferably less than 0.01 mole of the compound of formula (V).

DETAILED DESCRIPTION OF THE INVENTION

Figure 1:
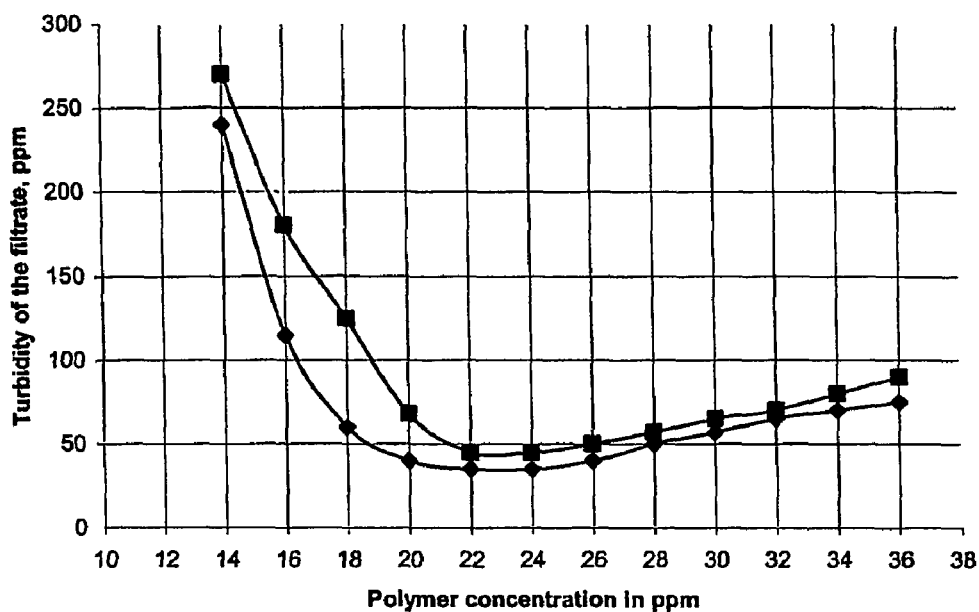
FIG. 1 shows filtrate turbidity as a function of polymer concentration at pH 7.02.

The process for manufacturing a polymer comprising units derived from at least one (meth)acrylate di-ammonium salt of formula (I) comprises the further step (c) of polymerising at least the compound of formula (I) contained in the solid product to achieve the polymer. When no compound of formula (V) is added to the monomer composition for producing the polymer, this polymer contains, per n units derived from at least one compound of formula (I), less than 0.1*n units, preferably less than 0.05*n units and more preferably less than 0.01*n units derived from at least one compound of formula (V).

It was found that, by an appropriate selection of the organic solvent, a selective separation of the (meth)acrylate di-ammonium salt from the mono-ammonium salt could be obtained notwithstanding the fact that both products are salts so that one would expect to achieve either a mixture in the solvent or a precipitation of both salts. Since no water has to be added to separate the di-ammonium salt from the reaction mixture, more than 2 equivalents of the compound of formula $R^3X$ can be added thereto to achieve, for a certain reaction time, a higher yield and/or purity and/or purity of the di-ammonium salt. Indeed, when adding water and more than 2 equivalents of the compound of formula $R^3X$, acid will be generated in the water causing a hydrolysis of the (meth)acrylate ester.

The present inventors have found that the (meth)acrylate di-ammonium salt obtained by the process according to the present invention can be easily co-polymerised with one or more other monomers in an amount higher than 10% by weight. In order to achieve polymers with increased charge densities, step (c) of the process according to the invention preferably comprises the co-polymerisation of from 12 to 99% by weight, preferably of from 20 to 99% by weight, of the compound of formula (I) contained in said solid product with from 1 to 88% by weight, preferably of from 1 to 80% by weight, of at least one further monomer.

The term "alkyl", as used herein, is defined as including saturated, monovalent hydrocarbon radicals having straight, branched or cyclic moieties or combinations thereof.

The term "aralkyl", as used herein, is defined as a radical of formula —$(CH_2)_n$-aryl wherein n is an integer from 1 to 4 and aryl means any aromatic hydrocarbon having 6 to 24 carbon ring atoms that may be monocyclic or annealed.

In this specification the term "(meth)acrylate" means "acrylate" as well as "methacrylate".

In the process according to the present invention, the organic solvent used in step (a) preferably contains at most 1000 ppm of water. The organic solvent used is preferably a solvent wherein the solubility of the di-ammonium salt of formula (I) has a solubility at 25° C. of less than 0.5 g/100 g of solvent.

In the process according to the present invention, the solvent used in step (a) is usually an aprotic dipolar solvent; preferably acetone, methylethylketone, ethylacetate, nitromethane, acetonitrile or mixtures thereof. Particularly preferred is acetonitrile. The reaction of step (a) is preferably carried out in an amount of between 500 and 5000 g of solvent per mole of the di-amino (meth)acrylate of formula (II) added to the solvent.

In the process according to the invention, step (a) is preferably carried out at a temperature ranging from 40 to 100° C., most preferably from 70 to 90° C. The process is preferably conducted at autogenic pressure in a closed reactor.

In the process according to the invention, step (a) is advantageously conducted with a molar ratio of the alkyl or aralkyl compound of formula $R^3X$ to the di-amino-(meth)acrylate of formula (II) higher than 2, most preferably of at least 2.1. The molar ratio preferably does not exceed 4.5, most preferably it does not exceed 3.

The duration of step (a) is generally from 1 to 100 hours, preferably from 10 to 30 hours.

The separation of solid product containing the (meth)acrylate di-ammonium salt of formula (I) in step (b) of the process according to the invention may be carried out by any means suitable for a mechanical separation. It is advantageously done by filtration or by centrifugation of the reaction mixture.

In an embodiment of the process according to the invention, the excess of alkyl or aralkyl derivative of formula $R^3X$ used in step (a) is separated from the reaction mixture, for example by stripping, before effectuating the separation in step (b).

The process according to the invention can be done as batch or continuously. In the latter case, the solid product containing the (meth)acrylate di-ammonium salt of formula (I) formed during step (a) can be separated from the reaction mixture continuously, for example by filtration, decantation or any other mean suitable therefore, and the reaction mixture can then be recycled and used as solvent in a subsequent reaction step (a).

According to another preferred embodiment of the process, the reaction mixture obtained after step (b) is recycled. In this embodiment, it is particularly preferred that the reaction mixture obtained after step (a) is filtered in step (b) in order to separate the solid product containing the (meth)acrylate di-ammonium salt of formula (I) already formed and to recycle the filtrate in a subsequent step (a) in order to continue the reaction. This recycling operation can be repeated several times. The recycling of the filtrate permits to increase even more the yield and the purity of the (meth)acrylate di-ammonium salt of formula (I).

In a variant of the process according to the invention, both embodiments are combined.

The di-amino (meth)acrylate of formula (II) used in step (a) of the process according to the invention can be obtained by any process suitable therefore. It is preferably obtained by the transesterification of a 1,3-di-amino-2-propanol of formula (III)

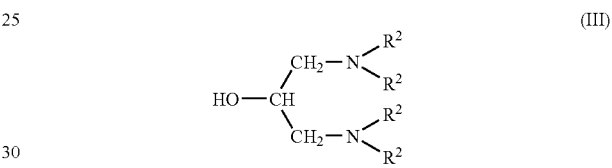

(III)

wherein each $R^2$, independently, represents an alkyl comprising from 1 to 4 carbon atoms, with a (meth)acrylate of formula (IV)

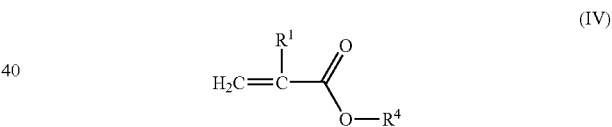

(IV)

wherein $R^4$ represents an alkyl comprising from 1 to 4 carbon atoms, in the presence of a lithium-based catalyst. It was found that the transesterification conducted with the aid of a lithium-based catalyst permitted to obtain high purity di-amino-(meth)acrylates with high yields. The synthesis of di-amino-(meth)acrylate of formula (II) has already been described in U.S. Pat. No. 3,586,711, in FR1568382, in FR1529000, in Zh.Org.Khim. 1969, 5(11), p. 1947-1952, and in US 2002/183543 (=EP 1254891). Di-amino-(meth)acrylate of formula (II) produced in accordance with these patent publications can be used in the process according to the present invention for preparing the (meth)acrylate di-ammonium salts. However, it was found that the process described in these documents gave relatively moderate yields. Moreover, the reaction temperatures necessary for conducting these processes were high so that often uncontrolled side-reactions and polymerisation occurred. It was surprisingly found that using a lithium-based catalyst could overcome these problems.

The present invention therefore also relates to a process for the manufacture of a di-amino-(meth)acrylate of formula (II) by the transesterification of a 1,3-di-amino-2-propanol of formula (III)

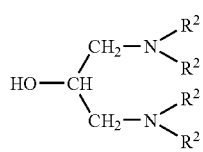

(III)

wherein each $R^2$, independently, represents an alkyl comprising from 1 to 4 carbon atoms, with a (meth)acrylate of formula (IV)

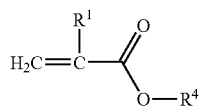

(IV)

wherein $R^4$ represents an alkyl comprising from 1 to 4 carbon atoms, in the presence of a lithium-based catalyst.

In this process for the manufacture of a di-amino-(meth) acrylate of formula (II), the lithium based catalyst is preferably chosen from lithium oxide ($Li_2O$), lithium hydroxide (LiOH), lithium carbonate ($Li_2CO_3$), lithiumalkoxides such as methoxylithium ($LiOCH_3$), tertiobutoxylithium (LiOtBu), the lithium salt of a 1,3-dialkyl amino-2-propanol corresponding to formula (III), lithium citrate, lithium chloride (LiCl), Li-stearate ($LiC_{18}H_{35}O_2$), $LiClO_4$, $Li_2SO_4$, LiOAc, LiOOCPh and/or lithium bromide (LiBr) and their mixtures. Especially preferred are lithiumoxide, lithiumhydroxide and lithiumalkoxides, especially lithium methoxide, and their mixtures.

In this transesterification process, the lithium-based catalyst is generally used in an amount of 1 to 20, preferably in an amount of 4 to 10, equivalents of Li per mole of 1,3-di-amino-2-propanol of formula (III).

In this transesterification process, the temperature is preferably not exceeding 120° C., more preferably the temperature is lower than 110° C. The transesterification is advantageously carried out at a temperature of at least 80° C.

The transesterification process is generally conducted at a pressure adapted to the desired reaction temperature.

The transesterification process is preferably carried out in the presence of from 500 to 3000 ppm (relative to the total weight of reaction mixture) of at least one stabiliser, preferably selected from radical inhibitors such as quinones, hydroquinones, phenothiazine, tris(nonylphenyl) phosphite. Preferred stabilisers are methyl ether of hydroquinone, phenothiazine, tris(nonylphenyl)phosphite, N,N'-diphenyl-1, 4-phenylenediamine, ethylenediaminetetraacetic acid and their mixtures. The transesterification process is generally carried out with a (meth)acrylate of formula (IV) to 1,3-di-amino-2-propanol of formula (III) molar ratio of from 1 to 10, preferably from 3 to 6.

The transesterification process is preferably conducted by introducing progressively the di-amine of formula (III) to the reaction mixture containing the catalyst and the (meth)acrylate of formula (IV) so that the formation of side-products is even more reduced.

(Meth)acrylates of formula (IV) wherein $R^4$ is methyl or ethyl, especially methyl, are preferred.

The di-amine (meth)acrylates of formula (II) obtained after the transesterification reaction are preferably isolated from the reaction mixture by distillation, more preferably under vacuum, and most preferably after removal of the lithium-based catalyst, for example by filtration and/or adsorption on silica.

The di-amino-(meth)acrylates of formula (II) are preferably stabilised by the addition thereto of less than 500 ppm of one or more stabilisers as described here above.

In the process according to the invention, compounds of formula (I), (II) and (IV) wherein $R^1$ is methyl are especially preferred.

In the process according to the invention, compounds of formula (I), (II) and (III) wherein $R^2$ is methyl are especially preferred.

In the process according to the invention, (meth)acrylate di-ammonium salts of formula (I) wherein each $R^3$, independently, is an alkyl comprising from 1 to 4 carbon atoms or benzyl, are preferred. Most preferred are compounds wherein each $R^3$, independently, is methyl or benzyl; especially methyl. (Meth)acrylate di-ammonium salts of formula (I) wherein both $R^3$ are the same are preferred.

In the process according to the invention, (meth)acrylate di-ammonium salts of formula (I) wherein each X, independently, is an anion selected from halides, especially chloride and bromide, and methylsulfonates are preferred. Especially preferred is chloride.

The process according to the invention permits to obtain a high yield of the desired (meth)acrylate di-ammonium salts of formula (I). Yields of at least 90, even 99, % can be obtained, resulting in 99+ pure (meth)acrylate di-ammonium salts of formula (I). Almost no side products are formed. In the final product the amount of impurities such as alkylhalogenides, alcohol and acids that could disturb further polymerisation of the product, are very low. The quantity of amino-(meth)acrylate ammonium salt of formula (V) (relative to the amount of di-ammonium salt of formula (I)) in the final product is very low, usually less than 10 mole %, preferably less than 5 mole %, or even less than 1 mole %.

Moreover, the process permits to obtain the products in pure solid form. In this form the products show high stability and can be stored for long periods without decomposition. Once the solid product is isolated, aqueous solutions and formulations with other monomers can be made as required for the envisaged application.

The present invention therefore also relates to a solid product which is obtainable by the (meth)acrylate di-ammonium salt manufacturing process according to the invention and which contains the (meth)acrylate di-ammonium salt of formula (I) and, per mole of this salt, less than 0.1 mole, preferably less than 0.05 mole and more preferably less than 0.01 mole, of the corresponding amino-(meth)acrylate ammonium salt of formula (V).

When used for the manufacture of polymers it is preferred to use products as pure as possible so that the nature of the polymer obtained can be controlled, and also to avoid the presence of impurities that can disturb the polymerisation. It has been found that the solid products containing the (meth) acrylate di-ammonium salts according to the present invention satisfy these requirements. The present invention therefore also relates to the use of the solid products containing the (meth)acrylate di-ammonium salts according to invention for the manufacture of polymers comprising less than 10 mole % (preferably less than 5 mole %, more preferably less than 1 mole %) of units derived from an amino-(met)acrylate ammonium salt of formula (V) and to the polymers which can thereby be obtained.

The present invention also relates to a polymer obtainable by the polymer manufacturing process according to the invention. These polymers are characterised by the fact that they contain units derived from at least one (meth)acryl di-ammonium salt of formula (I) and, per n units derived from this di-ammonium salt, less than 0.1*n, preferably less than 0.05*n and more preferably less than 0.01*n units derived from at least one amino-(meth)acrylate ammonium salt of formula (V) and/or by the fact that they contain of from 12 to 99% by weight, preferably of from 20 to 99% by weight, of units derived from at least one (meth)acryl di-ammonium salt of formula (I) and from 1 to 88% by weight, preferably of from 1 to 80% by weight, of units derived from at least one further monomer.

In the polymer manufacturing process according to the invention the polymerisation step (c) preferably comprises the step of co-polymerising of from 1 to 99 parts, preferably from 2 to 70 parts, by moles of the (meth)acrylate di-ammonium salt of formula (I) contained in the solid product separated from the reaction mixture with from 1 to 99 parts, preferably from 30 to 98 parts, by moles of at least one acrylamide monomer of formula (VI)

$$H_2C=C(R^5)-C(=O)-N(R^6)(R^7) \quad (VI)$$

wherein $R^5$ is hydrogen or methyl, $R^6$ and $R^7$ are, independently, hydrogen, alkyl comprising from 1 to 6 carbon atoms, optionally substituted by one or more hydroxy or alkoxy groups.

The acrylamide monomer of formula (VI) is preferably acrylamide.

In the manufacturing process of the polymers according to the invention use may further be made of:

(c) from 0 to 60 parts by moles of at least one water-soluble monomer which is potentially anionic by varying the pH, and which is preferably chosen from ethylenically unsaturated carboxylic acids and salts thereof and ethylenically unsaturated sulphonated monomers and salts thereof (such as acrylic acid, 2-acrylamido-2-methylpropanesulfonic acid and salts thereof);

(d) from 0 to 90 parts by moles of at least one cationic water-soluble monomer of formula (VII)

$$H_2C=C(R^8)-C(=O)-A-B-N^+(R^{11})(R^9)(R^{10}) \; Y^- \quad (VII)$$

wherein $R^8$ is hydrogen or methyl, A is —O— or —NH—, B is —CH$_2$—CH$_2$—, —CH$_2$—CH$_2$—CH$_2$— or —CH$_2$—CHOH—CH$_2$—, $R^9$ and $R^{19}$ are, independently, an alkyl comprising from 1 to 16 carbon atoms, $R^{11}$ is hydrogen or an alkyl comprising from 1 to 16 carbon atoms, and Y is a monovalent anion (such as (meth)acrylamidopropyltrimethylammonium and (meth)acryloyl-oxyethyltrimethylammonium halides);

(e) from 0 to 10 parts by moles of at least one hydrophobic monomer, preferably chosen from alkyl(meth)acrylates and vinylaromatic monomers (such as ethylacrylate, butylacrylate, styrene), and/or (f) from 0 to 30 parts by moles of at least one water-soluble monomer other than (a), (b), (c) and (d), preferably chosen from polyethoxylated (meth)acrylates, polyethoxylated (meth)acrylates containing hydrophobic units or aryl units and N-vinylpyrrolidone.

Based on the (meth)acrylate di-ammonium salt containing solid products according to the invention, polymers and copolymers of high molecular weight can be obtained, for example by solution polymerisation or polymerisation in dispersed media (emulsion and suspension). Preferred ways for the preparation of such polymers are inverse emulsion and suspension polymerisation processes. By inverse macroemulsion polymerisation, high molecular weight cationic acrylamide-based co- and terpolymers with different charges can be obtained.

It was found that the polymerisation rate of the (meth) acrylate di-ammonium salts obtained by the process according to the invention was quite high and that practically no residual cationic monomers were detected after 3 hours of polymerisation. The acrylates were more reactive compared to the methacrylates. The polymerisations proceeded smoothly with good temperature control.

The obtained polymers have a high molecular weight, generally at least 7.000.000 g/mol (based on intrinsic viscosity measurements in 0,5 mol/l NaCl at 25° C.).

The emulsions obtained had a high percentage of active material (40 wt %) and were free of coagulum.

It was found that more than 90% of the cationic monomers were accessible in the polymer.

The polymers according to the invention were therefore very useful for different purposes, and in general for whatever aqueous solid-liquid separations are required. They can be used in ion-exchange resins, for coatings, in personal care products, in cosmetics, as fabric softener, as biocide, as coagulant, as dye fixative, in oil field chemicals, in dispersants or as surfactants. They can also be used for fine retention in paper making, as flocculants, in the purification of municipal and industrial waste waters, in mines, quarries and drilling muds, in the assisted recovery of petroleum and in drinking water treatment, as stabilisers for emulsion polymerisation and in pharmaceuticals.

The polymers according to the invention showed good results when used as flocculants, especially for the treatment of industrial and municipal waste water. The present invention also relates to the use of a polymer according to the invention as flocculant.

The invention is further illustrated by the following examples:

The following abbreviations are used:

AM: acrylic acid methylester

MAM: methacrylic acid methylester

MeOH: methanol

MeCl: methylchloride

BzCl: benzylchloride

BDMAP: 1,3-bis(dimethylamino)-2-propanol

BDMAPA: 1,3-bis(dimethylamino)-2-propyl acrylate

BDMAPMA: 1,3-bis(dimethylamino)-2-propyl methacrylate

BDMAPA.2MeCl: 1,3-bis(trimethylammonium)-2-propyl acrylate chloride

BDMAPMA.2MeCl: 1,3-bis(trimethylammonium)-2-propyl methacrylate chloride

BDMAPA.MeCl: 1-(dimethylamino)-3-(trimethylammonium)-2-propyl acrylate chloride

BDMAPMA.MeCl: 1-(dimethylamino)-3-(trimethylammonium)-2-propyl methacrylate chloride BDMAPA.2BzCl: 1,3-bis(benzyldimethylammonium)-2-propyl acrylate chloride BDMAPMA.2BzCl: 1,3-bis(benzyldimethylammonium)-2-propyl methacrylate chloride BDMAPA.BzCl: 1-(dimethylamino)-3-(benzyldimethylammonium)-2-propyl acrylate chloride BDMAPMA.BzCl: 1-(dimethylamino)-3-(benzyldimethylammonium)-2-propyl acrylate chloride MEHQ: methyl ether of hydroquinone PTZ: phenothiazine TNPP: tris(nonylphenyl)phosfite DPPD: N,N'-diphenyl-1,4-phenylenediamine EDTA: ethylenediaminetetraacetic acid DBTO: dibutyltinoxide Example 1

Synthesis and Purification of
1,3-Bis(dimethylamino)-2-propyl methacrylate

The transesterification reaction is performed in a 3 liter jacketed glass reactor (Sovirel), equipped with a stirrer, temperature probe, air sparge and an adiabatic column filled with 7 structured metal gauze packings (Sulzer type DX). Distillation rate is controlled by a temperature controlled reflux set-up, with water-cooled condenser, on top of this column.

The reactor is loaded with 1950 g MAM (19.5 moles), 1.4 g MEHQ, 1.4 g PTZ and 1.4 g TNPP. This mixture is heated to reflux (96° C.), at atmospheric pressure and 95 g MAM containing traces of water are distilled off. 4.5 g dry $Li_2O$ (0.15 moles) is added. The reactor is heated with oil, at a temperature 25° C. higher, compared to the reaction mixture, and 3 liters/hour air is sparged through a sintered metal diffuser. Over a period of 100 minutes 447 g BDMAP (3.06 moles) are introduced. The methanol produced by the transesterification is distilled of at 78-94° C. at a reflux ratio 5/1-15/1. In total 755 g MeOH/MAM is collected containing 97 g (3.03 moles) MeOH. The reaction takes about 6 hours. Mass temperature in the reactor reaches 108-110° C. at the end. Part of the excess MAM is distilled to eliminate the last traces of MeOH. The cooled reaction mixture is passed on a Buchner filter covered with a thin layer of silica (Merck Silicagel 60) to remove the catalyst. At this stage the conversion of BDMAP is 98% and the yield of BDMAPMA 95%. (determined by GC). MAM is removed by distillation at a maximum boiler temperature of 65° C., by increasing vacuum from 20 up to 2 kPa. The obtained reaction mixture (663 g) is purified in a fractional distillation set-up, equipped with a column containing 16 structured SS packings (Sulzer DX) at 0.5 kPa. A top fraction of 31 g is obtained between 60-91.5° C. (reflux ratio 10/1) containing BDMAP and BDMAPMA to be recycled. Heart cut 518 g (2.4 moles)(>99.5% pure) BDMAPMA is distilled at 91.5° C. (reflux ratio 1/1); the bottom temperature'increases from 105° C. till 110° C.

The collected product is stabilised with 500 ppm MEHQ.

The distillation residue (102 g) still contains about 60% BDMAPMA.

Examples 2 to 6 and Comparative Examples 7 to 14

The transesterification, described in example 1, was repeated in other conditions and with a series of other catalysts. The results are shown in Table 1.

TABLE 1

| N° | Catalyst | Weight % on BDMAP | MAM/BDMAP (molar) Addition mode* | Max T (° C.) | Conv. BDMAP (%) | Molar yield BDMAPMA (%) | Sum of Michael Addition Products % molar |
|---|---|---|---|---|---|---|---|
| 1 | $Li_2O$ | 1 | 6 C | 110 | 98 | 95 | 2 |
| 2 | $Li_2O$ | 0.5 | 5 B | 107 | 85 | 81 | 4 |
| 3 | $Li_2O$ | 2 | 5 C | 112 | 98 | 85 | 8 |
| 4 | $Li_2O$ | 1 | 5 B | 110 | 95 | 90 | 5 |
| 5 | $LiOCH_3$ | 1 | 5 B | 109 | 94 | 80 | 10 |
| 6 | LiOH | 1 | 6 B | 110 | 95 | 85 | 6 |
| 7 | $NaOCH_3$ | 1 | 6 B | 109 | 11 | 8 | nd |
| 8 | Ca-acetyl-acetonate | 1 | 5 B | 107 | 0 | 0 | nd |
| 9 | DBTO Tegokat23 | 1.5 | 5 B | 105 | 0 | 0 | nd |
| 10 | DBTO Tegokat 248 | 1.5 | 5 B | 106 | 5 | 2 | nd |
| 11 | Octabutyl-tetrachloro di-stannoxane | 1 | 5 B | 107 | 0 | 0 | nd |
| 12 | Dibutyl-dioctyl tetrachloro-di-stannoxane | 1 | 5 B | 107 | 0 | 0 | nd |
| 13 | Titanium-(IV)ethoxide | 1 | 5 B | 110 | 0 | 0 | nd |
| 14 | Titanium-(IV)-isopropoxide | 1 | 5 B | 110 | 0 | 0 | nd |

(*Mode C = Continuous addition of BDMAP; Mode B = BDMAP is loaded batch-wize, nd: not determined)

Only the Lithium containing catalysts proof to be good transesterification catalysts. Almost no or no reaction was observed when using sodium methylate, alkyltitanates or tin catalysts at temperatures below 115° C. At higher temperatures polymerisation occurred despite the addition of inhibitors.

Example 15

Synthesis and Purification of
1,3-Bis(dimethylamino)-2-propyl acrylate

In the same equipment as example 1, 2000 g (20 moles) Ethylacrylate, 1.4 g MEHQ, 1.4 g PTZ and 1.4 g TNPP are introduced, 3 l/h air sparge is installed. Traces of water are removed by distillation of 120 g ethylacrylate at 80° C./75 kPa. 4.5 g dry $Li_2O$ (0.15 moles) is added. Over a period of 2 hours, 447 g BDMAP (3.06 moles) are introduced. The ethanol produced (~3 moles) is distilled off together with part of the ethylacrylate at a temperature, between 66-80° C./75 kPa at top of the distillation column, maximum temperature in the boiler reaches 102° C. After 11 hours the mixture is cooled down and filtered over silica. At this stage the conversion of BDMAP is 93% and the yield of BDMAPA reaches 87% (determined by GC). 1.5 g DPPD is added, and ethylacrylate is distilled off at reduced pressure (20 to 2 kPa). 750 g reaction mixture containing 530 g BDMAPA is distilled in the same fractional distillation set-up as described in example 1, at 0.4 kPa. 426.5 g (2.13 moles)>99% pure BDMAPA (GC) is obtained as heart cut at 0.4 kPa and 80° C.

Examples 16 to 17 and Comparative Examples 18 to 21

The transesterification, described in example 15, was repeated in other conditions and with a series of other catalysts. The results are shown in Table 2.

TABLE 2

| N° | Catalyst, % weight on BDMAP | Alkyl-acrylate | Hours Mode* feed BDMAP | Max T (° C.)/ Press. in kPa | Conv. BDMAP % | Molar yield BDMAPA % | Michael Addition Products % |
|---|---|---|---|---|---|---|---|
| 15 | $Li_2O$ 1% | Ethyl | 11 C | 102/75 | 93 | 87 | 6 |
| 16 | $LiOCH_3$ 1.25% | Ethyl | 11 C | 100/75 | 97 | 77 | 12 |
| 17 | $LiOCH_3$ 2% | Methyl | 5 B | 80/80 | 95 | 60 | 30 |
| 18 | BaO 2% | Ethyl | 4 B | 97/75 | 85 | 18 | 25 |
| 19 | $NaOCH_3$ 1% | Methyl | 6 B | 90/101 | 0 | 0 | nd |
| 20 | Ca-acetylacetonate 2% | Methyl | 6 B | 87/101 | 0 | 0 | nd |
| 21 | DBTO Tegokat 23 2% | Ethyl | 6 B | 98/77 | 0 | 0 | nd |

(*Mode C = Continuous addition of BDMAP; Mode B = BDMAP is loaded batch-wize) nd: not determined Examples 22-23

Synthesis of 1,3-Bis(dimethylamino)-2-propyl acrylate Under Pressure

To obtain reaction temperatures above 100° C., the transesterification of AM with BDMAP, such as described in example 15 with ethylacrylate, was repeated under pressure. The results are shown in Table 3. The equipment described in example 1 was constructed in 316 SS for these trials. BDMAP was added by means of a dosing pump.

TABLE 3

| N° | Catalyst % weight on BDMAP | Acrylate | Hours Mode feed* BDMAP | Max T (° C.)/ Press in kPa | Conv. BDMAP | Molar yield BDMAPMA | Michael Addition Products |
|---|---|---|---|---|---|---|---|
| 22 | $Li_2O$ 1% | AM | 5 C | 103/135 | 92 | 53 | 25 |
| 23 | $LiOCH_3$ 1.5% | AM | 6 C | 104/135 | 95 | 61 | 20 |

(*Mode C = Continuous addition of BDMAP; Mode B = BDMAP is loaded batch-wize)

Examples 24 to 28

Reaction of BDMAPMA with Methylchloride

The quaternization reactions 24 to 28 are performed in a 2 liter, jacketed glass autoclave (Büchi AG), equipped with a stirrer, plunger, temperature and pressure probe and equipped with a bottom valve.

In example 28, to 193 g (0.9 moles) BDMAPMA in 800 g acetonitrile, 115 g (2.27 moles) methylchloride are added over a period of one hour. The mixture is heated up to 82° C., the pressure rises to 2 bar.

A white solid starts to precipitate. After 23 hours at 80-82° C. the mixture is cooled to room temperature, the excess of MeCl is stripped with nitrogen and the solid is filtered over a pressure filter. After drying with air and 4 hours under reduced pressure (10 kPa), 285 g BDMAPMA.2MeCl are obtained. (see table 4).

From this BDMAPMA.2MeCl, aqueous solutions can be made up to 50% weight. These solutions contain less than 100 ppm acetonitrile (GC headspace analysis).

Examples 24 to 27 are done according to the same procedure, except that the reaction conditions specified in Table 4 are used.

TABLE 4

| Nr | Acetone g | Aceto-nitrile g | BDMAPMA moles | MeCl Moles | Slurry % solids | T °C. | Reaction time (hours) | Powder weight (g) | Molar Yield % | Purity BDMAPMA•2MeCl % |
|----|-----------|-----------------|---------------|------------|-----------------|-------|-----------------------|-------------------|---------------|------------------------|
| 24 | 792.1 | — | 0.69 | 1.45 | 21 | 50 | 22 | 136 | 53.8 | 93.2 |
| 25 | 815.6 | — | 0.75 | 1.64 | 22 | 60 | 25 | 183 | 68.7 | 93.1 |
| 26 | 793.3 | — | 0.69 | 1.51 | 21 | 80 | 22 | 202 | 84.9 | 94.8 |
| 27 | — | 793 | 0.93 | 2.04 | 26 | 85 | 28 | 277 | 93.1 | 99.4 |
| 28 | — | 800 | 0.91 | 2.27 | 26 | 80 | 23 | 285 | 97.2 | 99.0 |

Examples 29-31

Reaction of BDMAPMA with Methylchloride and Recycling the Filtrate

The quaternization reactions 29 to 31 are performed in a 10 liter, SS Hofer autoclave in the same reaction conditions as example 28. The filtrate is reused in the following reaction.

TABLE 5

| nr | Recycle number | Aceto-nitrile g | BDMAPMA moles | MeCl Moles | Slurry % solids | T °C. | React time (hours) | Powder weight (g) | Molar Yield % | Purity BDMAPMA•2MeCl % |
|----|----------------|-----------------|---------------|------------|-----------------|-------|--------------------|-------------------|---------------|------------------------|
| 29 | — | 3923 | 3.50 | 8.75 | 21 | 72 | 22 | 1037 | 90.2 | 98.0 |
| 30 | Rec 1 | 3884 | 3.50 | 8.75 | 22 | 71 | 23 | 1095 | 96.0 | 99.5 |
| 31 | Rec 2 | 4015 | 3.50 | 8.75 | 22 | 73 | 24 | 1113 | 98.6 | 99.6 |

Examples 32 to 34

Quaternization of BDMAP(M)A with Benzylchloride or Methylchloride

Comparable results were obtained for the benzylchloride/BDMAPMA; methylchloride/BDMAPA and benzylchloride/BDMAPA reactions in the 2l reactor following the procedure of example 28.

The results are shown in Table 6.

TABLE 6

Quaternization of BDMAP(M)A with benzylchloride or methylchloride

| nr | Aceto-nitrile g | R-Cl | Moles | (meth)acryl-ate moles | Slurry % solids | T °C. | React time hours | Powder weight (g) | Molar Yield % | Purity % |
|---|---|---|---|---|---|---|---|---|---|---|
| 32 | 800 | MeCl | 1.72 | BDMAPA 0.69 | 18 | 80 | 23 | 205.0 | 97.7 | BDMAPA•2MeCl 99.5 |
| 33 | 1000 | BzCl | 1.45 | BDMAPMA 0.56 | 20 | 80 | 24 | 250.0 | 96.5 | BDMAPMA•2BzCl 99.6 |
| 34 | 1000 | BzCl | 1.45 | BDMAPA 0.56 | 20 | 80 | 24 | 245.0 | 96 | BDMAPA•2BzCl 99.1 |

Comparative Examples 35 and 36

For trials 35 and 36 the quaternization was realised in chloroform following the procedure described in patent WO 01/55089. The formed salts were extracted with water to form a ~50% aqueous solution.

TABLE 7

Quaternization of BDMAPMA with benzylchloride or methylchloride in chloroform

| nr | Chloro-form g | R-Cl | Moles | BD-MAPMA moles | Aq. sol. % | T C. | React time (h) | Press. kPa | Molar Yield % | Purity % | |
|---|---|---|---|---|---|---|---|---|---|---|---|
| 35 | 1234 | MeCl | 3.50 | 1.75 | 50 | 50 | 25 | 300 | 72.0 | BDMAPMA•2MeCl 75.4 | BDMAPMA•MeCl 24.6 |
| 36 | 1414 | BzCl | 4.0 | 2.0 | 48 | 52 | 25 | 100 | 84.7 | BDMAPMA•2BzCl 89.5 | BDMAPMA•BzCl 10.5 |

In our attempts to perform the quaternization with MeCl or BzCl in aqueous solution, partial hydrolysis was observed due to the longer reaction time (12-24 hours) for the quaternization of the second amine function. Pure bisquaternized products in solution could not be obtained and it is almost impossible to purify the obtained mixtures.

TABLE 8

Comparison of the impurities/purity of 50 wt % bisquaternized methacrylate monomer solutions in water

| Bisquaternized product from trial | R-Cl | % weight | methacrylic acid % weight |
|---|---|---|---|
| 31 | MeCl | — | 0.1 |
| 33 | BzCl | <0.1 | <0.05 |
| 35 | MeCl | — | 2.5 |
| 36 | BzCl | 0.3 | 1.3 |

Example 37

Inverse Emulsion Copolymerisation of BDMAPMA.2MeCl and Acrylamide

This procedure is typical for the synthesis of 1 kg copolymer emulsion with 40% active material, containing 25% BDMAPMA.2MeCl Preparation of the aqueous phase: to 300 g acrylamide dissolved in 182 g demineralized water, 200 g of a 50% aqueous solution of BDMAPMA.2MeCl, 0.2 g EDTA and 0.2 g potassium bromate were added. After stirring for 30 minutes 0.7 g lactic acid and 5 g adipic acid were added (pH=3.5).

Preparation of the oil phase: in a 2 liter SS beaker equipped with mechanical stirrer 240 g Isopar M (Isoparaffinic solvent, ExxonMobil), 18 g Montane 70 (Sorbitan mono isostearate, Seppic) and 4.6 g Atlas G-1086 (Polyoxyethylene sorbitol hexaoleate, Uniqema) were mixed.

The aqueous phase was transferred quickly to the oil phase under stirring. The mixture was emulsified for 30 seconds at 8000 rpm using a homogenizer.

Polymerisation: the resulting emulsion was introduced in a 1 liter explosion proof CEMCO reactor equipped with a 3 blade axial flow impeller, The emulsion was continuously purged with a nitrogen flow (1.5 l/min) for 45 minutes. At 40° C. a 0.5 g solution of 0.2 g azobis(2,4-dimethylvaleronitrile) catalyst in xylene was added through a septum on top of the reactor. The nitrogen flow was limited to 1 ml/min. The reaction was maintained at 40° C. for 2 hours, and then increased up to 48° C. in a time span of 3 hours, with reintroduction of 0.12 g catalyst after 3 hours and 4 hours of reaction. After 5 hours, 1.2 g of sodium metabisulfite in 3 g water was added and the reaction temperature was increased to 55° C. for 1 hour-. The resulting emulsion was free of acrylamide (less then 100 ppm), showed no coagulum content and had an intrinsic viscosity (IV) of 111:11/g. (See table 9)

Examples 38-46

The same procedure of example 37 was followed with varying amounts of acrylamide and monomers BDMAPMA.2MeCl or BDMAPA.2MeCl to obtain emulsions containing 40% active material. The results are represented in Table 9.

Terpolymers were also prepared in Examples 45 and 46 in the same way by using MAPTAC (Röhm) (methacrylamidopropyltrimethylammoniumchloride) and AOETAC (2-(acryloyloxy)ethyltrimethylammonium chloride, Mitsui Chemicals) as comonomers.

TABLE 9

| N° | Cationic monomer | Initial conc % | Intrinsic viscosity dl/g | Product viscosity cP | Cationic monomer in polymer % |
|---|---|---|---|---|---|
| 37 | BDMAPMA•2MeCl | 25 | 11.0 | 520 | 23.2 |
| 38 | BDMAPMA•2MeCl | 5 | 11.8 | 560 | 4.8 |
| 39 | BDMAPMA•2MeCl | 10 | 10.4 | 560 | 9.4 |
| 40 | BDMAPMA•2MeCl | 40 | 11.1 | 380 | 35.7 |
| 41 | BDMAPA•2MeCl | 5 | 12.6 | 400 | 4.8 |
| 42 | BDMAPA•2MeCl | 10 | 14.1 | 680 | 9.4 |
| 43 | BDMAPA•2MeCl | 25 | 10.3 | 540 | 23.1 |
| 44 | BDMAPA•2MeCl | 50 | 16.8 | 540 | 45.0 |
| 45 | BDMAPA•2MeCl MAPTAC | 5 5 | 11.4 | 560 | nd |
| 46 | BDMAPA•2MeCl AOETAC | 5 20 | 10.7 | 560 | nd | nd = not determined

The polymer obtained in Example 37 was tested for flocculation properties in a standard test with a kaolin suspension (6.6 g/l) and compared to commercial cationic polymers Alpinefloc™ E1+ (50% cationic monomer: AOETAC).

The turbidity of the filtrate was measured as a function of the polymer concentration.

Figure 2:
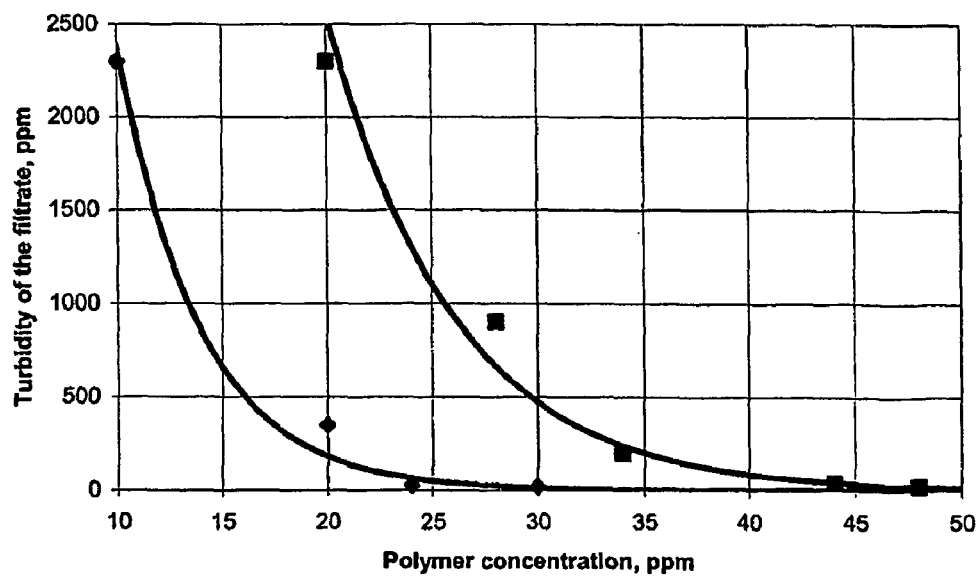
FIG. 2 shows filtrate turbidity as a function of polymer concentration at pH 8.

The results obtained at pH 7.02 and pH 8, respectively, are represented in FIGS. 1 and 2. In these figures, the results obtained with the polymer of Example 37 are labelled ♦; the results obtained with Alpinefloc™ E1+ are labelled ■.

These results show that better performances are obtained with the polymer of Example 37 with respect to the polymer concentration and the transparency of the filtrate than with commercial polymers containing more cationic monomers.

The invention claimed is:

1. Process for the manufacture of a (meth)acrylate di-ammonium salt of formula (I)

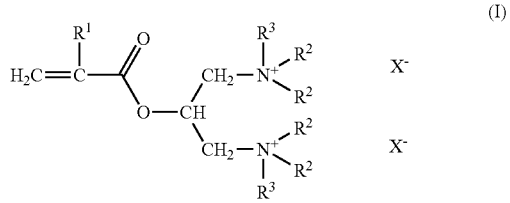

(I)

wherein $R^1$ represents hydrogen or methyl, each $R^2$, independently, represents a C1 to C4 alkyl, each $R^3$, independently, represents an alkyl or an aralkyl and each $X^-$, independently, represents an anion selected from the group consisting of halides and methylsulfonates, comprising (1) the reaction of the di-amino (meth)acrylate of formula (II)

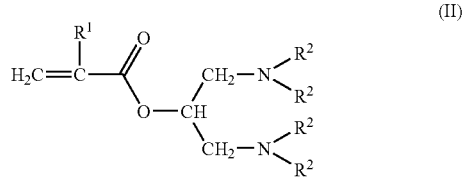

(II)

with at least one alkyl or aralkyl derivative of formula $R^3X$ in an aprotic dipolar organic solvent containing at most 5000 ppm of water and wherein the compound of formula (I) has a solubility at 25° C. of less than 1 g/100 g of solvent and wherein the solubility of the corresponding amino-(meth)acrylate ammonium salt of formula (V)

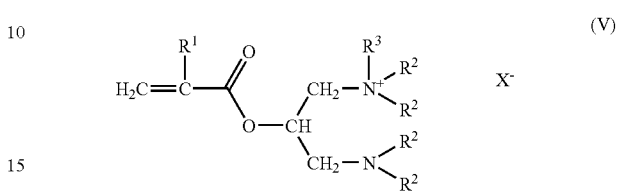

(V)

has a solubility at 25° C. of at least 20 g/100 g of solvent; and (2) the separation of the compound of formula (I) from the reaction mixture without dissolving it in water, the compound of formula (I) being separated from the reaction mixture in the form of a solid product comprising, per mole of the compound of formula (I), less than 0.1 mole of the compound of formula (V).

2. Process for the manufacture of a polymer which process includes the process of claim 1 and comprises the further step (3) of polymerising of at least the compound of formula (I) contained in said solid product to achieve said polymer.

3. Process according to claim 2, wherein step (3) comprises the co-polymerisation of at least 12% by weight of the compound of formula (I) contained in said solid product with at the most 88% by weight of at least one further monomer.

4. Process according to claim 2, wherein step (3) comprises a radical co-polymerisation of a water-based solution of monomers polymerised by emulsion or suspension techniques.

5. Process according to claim 2, wherein step (3) comprises the co-polymerisation of from 1 to 99 parts by moles of the compound of formula (I) contained in said solid product with from 1 to 99 parts by moles of at least one acrylamide monomer of formula (VI)

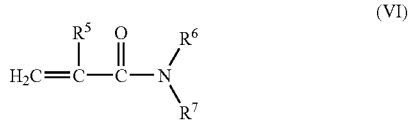

(VI)

wherein $R^5$ is hydrogen or methyl, $R^6$ and $R^7$ are, independently, hydrogen, or C1 to C6 alkyl, optionally substituted by one or more hydroxy or alkoxy groups.

6. Process according to claim 1, wherein the separation of the (meth)acrylate di-ammonium salt of formula (I) from the reaction mixture is done by mechanical separation.

7. Process according to claim 1, wherein the reaction mixture obtained after step (2) is recycled.

8. Process according to claim 1, wherein the di-amino (meth)acrylate of formula (II) used in step (1) is prepared by the transesterification of a 1,3-di-amino-2-propanol of formula (III)

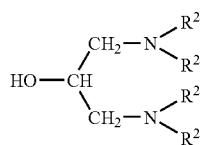

(III)

wherein each $R^2$, independently represents a C1 to C4 alkyl, with a (meth)acrylate of formula (IV)

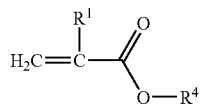

(IV)

wherein $R^1$ represents hydrogen or methyl and $R^4$ represents a C1 to C4 alkyl, in the presence of a lithium-catalyst.

9. Process according to claim 1, wherein X is Cl.

10. Process according to claim 1, wherein the di-amino (meth)acrylate of formula (II) is allowed to react in step (1) with more than 2 equivalents of said alkyl or aralkyl derivative of formula $R^3X$.

11. Process according to claim 1, wherein the reaction of step (1) is effectuated in an amount of between 500 and 5000 g of solvent per mole of the di-amino (meth)acrylate of formula (II).

12. Process according to claim 8, wherein the lithium catalyst is chosen from $Li_2O$, $LiOCH_3$, LiOH and their mixtures.

13. Process according to claim 8, wherein the transesterification is done at a temperature not exceeding 120° C.

14. Process according to claim 1, wherein $R^1$ is methyl.

15. Process according to claim 1, wherein $R^2$ is methyl.

16. Process according to claim 1, wherein $R^3$ is methyl.

17. Process according to claim 1, wherein $R^3$ is benzyl.

18. Process according to claim 8, wherein $R^4$ in formula (IV) is methyl.

19. Process according to claim 1, wherein said organic solvent contains at most 1000 ppm of water.

20. Process according to claim 1, wherein the solubility of the compound of formula (I) in said organic solvent is less than 0.5 g/100 g of solvent.

21. Process according to claim 1, wherein the solid product which is separated from the reaction mixture comprises, per mole of the compound of formula (I), less than 0.05 mole of the compound of formula (V).

22. Process according to claim 1, wherein the solid product which is separated from the reaction mixture comprises, per mole of the compound of formula (I), less than 0.01 mole of the compound of formula (V).

23. Process according to claim 1, wherein the solvent is selected from the group consisting of acetone, methylethylketone, ethylacetate, nitromethane, acetonitrile or mixtures thereof.

24. Process according to claim 23, wherein the solvent is acetonitrile.

25. Process according to claim 10, wherein the di-amino (meth)acrylate of formula (II) is allowed to react in step (1) with more than 2.1 equivalents of said alkyl or aralkyl derivative of formula $R^3X$.

* * * * *